United States Patent
Oshima et al.

(10) Patent No.: US 7,846,068 B2
(45) Date of Patent: Dec. 7, 2010

(54) ACTIVITY METER

(75) Inventors: Yoshitake Oshima, Kyoto (JP); Kaori Kawaguchi, Utsunomiya (JP); Ryosuke Doi, Kyoto (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 12/452,358

(22) PCT Filed: Jul. 15, 2008

(86) PCT No.: PCT/JP2008/062755

§ 371 (c)(1),
(2), (4) Date: Dec. 28, 2009

(87) PCT Pub. No.: WO2009/016960

PCT Pub. Date: Feb. 5, 2009

(65) Prior Publication Data

US 2010/0120584 A1    May 13, 2010

(30) Foreign Application Priority Data

Jul. 27, 2007    (JP) ............................. 2007-195614

(51) Int. Cl.
*A63B 71/00* (2006.01)

(52) U.S. Cl. .................. 482/8; 482/1; 482/4; 482/9; 482/901

(58) Field of Classification Search ................ 482/1–9, 482/900–902; 434/247; 463/37; 473/59; 600/300, 513

See application file for complete search history.

(56) References Cited

U.S. PATENT DOCUMENTS 4,699,379 A * 10/1987 Chateau et al. ............... 473/59

2008/0119330 A1 * 5/2008 Chiang et al. ................ 482/8
2010/0216601 A1 * 8/2010 Saalasti et al. ............... 482/8

FOREIGN PATENT DOCUMENTS

| JP | A-2001-087247 | 4/2001 |
| JP | A-2001-258870 | 9/2001 |
| JP | A-2005-270412 | 10/2005 |
| JP | A-2006-180899 | 7/2006 |
| JP | A-2006-204446 | 8/2006 |
| JP | B2-3880260 | 2/2007 |
| JP | A-2007-160076 | 6/2007 |

OTHER PUBLICATIONS

International Search Report issued in International Application No. PCT/JP2008/062755 on Oct. 21, 2008 (w/ English-language translation).

* cited by examiner

*Primary Examiner*—Glenn Richman
(74) *Attorney, Agent, or Firm*—Oliff & Berridge, PLC

(57) ABSTRACT

An activity meter includes a sensor for detecting acceleration in a plurality of directions, representative acceleration calculation means for calculating a representative acceleration based on an output signal of the sensor, and exercise intensity calculation means for calculating an exercise intensity of a body motion performed in the unit period from the representative acceleration. The exercise intensity calculation means includes a plurality of calculation formulas to use in the calculation of the exercise intensity, and determines the calculation formula to use in the calculation of the exercise intensity of the body motion performed in the unit period based on a horizontal component and a vertical component of the representative acceleration. The activity amount on various types of body activities from daily activity to exercise thus can be accurately measured.

13 Claims, 9 Drawing Sheets

ACTIVITY METER

TECHNICAL FIELD

The present invention relates to a technique of measuring a physical activity amount of a user.

BACKGROUND ART

A method of measuring exercise intensity and energy expenditure of a physical activity using an acceleration sensor is known (see Patent Documents 1 and 2). In a device of Patent Document 1, a standard deviation Sw of acceleration at a constant time tw is calculated from an output signal of the acceleration sensor, and exercise intensity wi is calculated from the standard deviation Sw using a conversion formula prepared in advance. In a device of Patent Document 2, an impulse of an exercise mass is calculated by vector synthesis from the acceleration of three axes, and the energy expenditure is calculated from the impulse in correspondence to a type of exercise. The type of exercise is determined based on the ratio of the impulse by synthesized vector and the impulse in the front and back, left and right, and up and down directions.

[Patent Document 1] Japanese Unexamined Patent Publication No. 2006-204446
[Patent Document 2] Japanese Unexamined Patent Publication No. 2001-258870

DISCLOSURE OF THE INVENTION

Problems to be Solved by the Invention

In recent years, the proportion of lifestyle-related diseases such as ischemic heart disease, cerebrovascular disease, and diabetes occupying the entire disease is increasing and becoming a major problem. In order to reduce the developing risk of such lifestyle-related diseases, reconsidering the undesirable lifestyle such as lack of exercise to improve metabolic syndrome (visceral fat syndrome), which is a basic clinical condition, is known to be effective.

As a specific guideline, the reference value of the physical activity amount for health promotion is defined as "23 exercises (METs·hour) pre week by the physical activity with intensity of greater than or equal to 3 METs, of which 4 exercises by the exercise with intensity of greater than or equal to 3 METs" in "Exercise and Physical Activity Reference for Health Promotion 2006" and "Exercise and Physical Activity Guide for Health Promotion 2006 (Exercise Guide 2006)" reported as one of exercise measures of Ministry of Health, Labor and Welfare. The "physical activity" refers to all bodily movement that accompanies energy expenditure above resting energy expenditure, and the "exercise" refers to a kind of physical activities that are performed in a planned and intended manner in an aim of maintaining and enhancing the physical strength. Other than the exercise of the physical activities is referred to as a "daily activity".

As apparent from such guidelines, needs to measure and manage the physical activity amount not only for exercise such as walking and jogging but also for daily activity such as cleaning and doing laundry is assumed to arise in the future.

Since the body movement clearly differs for the daily activity and for the exercise, the algorithm (calculation formula) for obtaining the physical activity amount from the acceleration information also obviously differs. However, the conventional device cannot distinguish the daily activity from the exercise and thus needed to apply the same algorithm for both, which leads to lowering in the measurement accuracy of the physical activity amount as a result.

The present invention has been devised to solve the problems described above, and an object thereof is to provide a technique capable of accurately measuring the activity amount for various types of physical activities from daily activity to exercise.

Means for Solving the Problems

The present invention adopts the following configuration to achieve the above object.

An activity meter according to a first aspect of the present invention includes a sensor for detecting acceleration in a plurality of directions; representative acceleration calculation means for calculating a representative acceleration, which is a representative value of the acceleration in a unit period, based on an output signal of the sensor; and exercise intensity calculation means for calculating an exercise intensity of a body motion performed in the unit period from the representative acceleration. The exercise intensity calculation means includes a plurality of calculation formulas to use in the calculation of the exercise intensity, and determines the calculation formula to use in the calculation of the exercise intensity of the body motion performed in the unit period based on a horizontal component and a vertical component of the representative acceleration. In this case, preferably, the activity meter further includes number of steps calculation means for calculating number of steps in the unit period based on the output signal of the sensor, wherein the exercise intensity calculation means determines the calculation formula to use in the calculation of the exercise intensity of the body motion performed in the unit period based on the number of steps, and the horizontal component and the vertical component of the representative acceleration.

The vertical component of the acceleration tends to greatly appear in exercises such as walking and jogging than in daily activities. The present invention focuses on such an aspect, and determines the type of physical activity by evaluating "the horizontal component and the vertical component of the representative acceleration". However, the daily activity and the exercise are sometimes difficult to clearly separate with only the evaluation of "the horizontal component and the vertical component of the representative acceleration". Thus, "the horizontal component and the vertical component of the representative acceleration" and "the number of steps" are preferably evaluated in combination. This focuses on the tendency that the number of steps becomes large in exercises performed in a planned and intended manner than in daily activities. The type of physical activity can be accurately determined and a more appropriate calculation formula can be selected by evaluating the two indices. The "horizontal component and the vertical component of the representative acceleration" are preferably evaluating using the ratio, the difference, and the like of the horizontal component and the vertical component.

For example, preferably, the exercise intensity calculation means includes at least a calculation formula for the exercise and a calculation formula for the daily activity for the calculation formula, the calculation formula for the exercise is selected when a value of a ratio of the vertical component with respect to the horizontal component of the representative acceleration is greater than or equal to a first threshold value, the calculation formula for the daily activity is selected when the value of the ratio is smaller than a second threshold value, and the calculation formula for the exercise or the calculation formula for the daily activity is determined depending on whether or not the number of steps is greater than or equal to a third threshold value when the value of the ratio is greater than or equal to the second threshold value and smaller than the first threshold value.

The activity meter preferably includes a filter for removing a fluctuation component of a static acceleration from the output signal of the sensor. The influence of gravitational acceleration thus can be removed, and the change in the dynamic acceleration due to the body motion of the user can be grasped.

The sensor is preferably a sensor that does not detect change in a static acceleration and detects only change in a dynamic acceleration. According to this type of sensor, the body motion of the user can be accurately grasped without arranging the filter.

An activity meter according to a second aspect of the present invention includes a sensor for detecting acceleration in a plurality of directions; representative acceleration calculation means for calculating a representative acceleration, which is a representative value of the acceleration in a unit period, based on an output signal of the sensor; and exercise intensity calculation means for calculating an exercise intensity of a body motion performed in the unit period from the representative acceleration. The exercise intensity calculation means includes a plurality of calculation formulas to use in the calculation of the exercise intensity, and determines the calculation formula to use in the calculation of the exercise intensity of the body motion performed in the unit period based on change in tilt of a body.

In this case, the exercise intensity calculation means preferably determines a value representing the change in the tilt of the body based on a value representing a fluctuation component of a static acceleration and a value representing a fluctuation component of a dynamic acceleration contained in the output signal of the sensor.

In the case of exercise such as walking and jogging, the tilt of the body (orientation of the sensor) barely changes. In other words, the fluctuation of the static acceleration barely appears in the output signal of the sensor. In the case of daily activity such as cleaning and doing laundry, on the other hand, the change in the tilt of the body (orientation of the sensor) becomes often since the operation of tilting or bending the upper body is performed, whereby the fluctuation of the static acceleration (gravitational acceleration) tends to appear in the output signal of the sensor. Therefore, the type of physical activity can be accurately determined and an appropriate calculation formula can be selected by evaluating the fluctuation component of the static acceleration.

Preferably, the activity meter includes a filter for removing a fluctuation component of a static acceleration from the output signal of the sensor, wherein a first representative acceleration is calculated from an output signal of before passing the filter, a second representative acceleration is calculated from an output signal of after passing the filter, and a value representing the change in the tilt of the body is determined based on the first representative acceleration and the second representative acceleration.

Preferably, the exercise intensity calculation means includes at least a calculation formula for the exercise and a calculation formula for the daily activity for the calculation formula, the calculation formula for the exercise is selected when the value representing the change in the tilt of the body is smaller than a fourth threshold value, and the calculation formula for the daily activity is selected when the value representing the change in the tilt of the body is greater than or equal to the fourth threshold value.

The value representing the change in the tilt of the body is preferably determined based on a horizontal component and a vertical component of the representative acceleration.

Preferably, the exercise intensity calculation means includes a calculation formula for resting for the calculation formula, and the exercise intensity is calculated using the calculation formula for resting when the representative acceleration is smaller than a fifth threshold value. The exercise intensity during rest also can be accurately calculated.

In the present invention, "unit period" refers to a period that becomes the unit in the calculation of the exercise intensity, and can be appropriately set from a range of about a few seconds to a few minutes. The "representative value of the acceleration in the unit period" refers to a statistics value obtained from the values of a plurality of accelerations sampled from the unit period. Any value such as an average (arithmetic average, geometric average), a maximum value, a minimum value, an intermediate value, a deviation, a standard deviation, or an average deviation may be used for the representative value.

The representative acceleration calculation means calculates the representative value of the acceleration in each direction from the output signal of the sensor, and synthesizes the representative value of each direction to calculate the "representative acceleration". Here, each direction is typically the vertical direction (up and down direction) and the horizontal direction (up and down direction, left and right direction), but is not limited thereto. When the "representative acceleration" is calculated by synthesizing the representative values of the acceleration in the vertical direction and the horizontal direction, "the representative value of the acceleration in the vertical direction" can be handled as "the vertical component of the representative acceleration", and "the representative value of the acceleration in the horizontal direction" can be handled as "the horizontal component of the representative acceleration". It should be recognized that the vertical component and the horizontal component can be calculated by breaking up the calculated "representative acceleration" to the vertical direction and the horizontal direction.

Effects of the Invention

According to the present invention, the activity amount for various types of physical activities from daily activity to exercise can be accurately measured.

DESCRIPTION OF SYMBOLS

Figure 1:
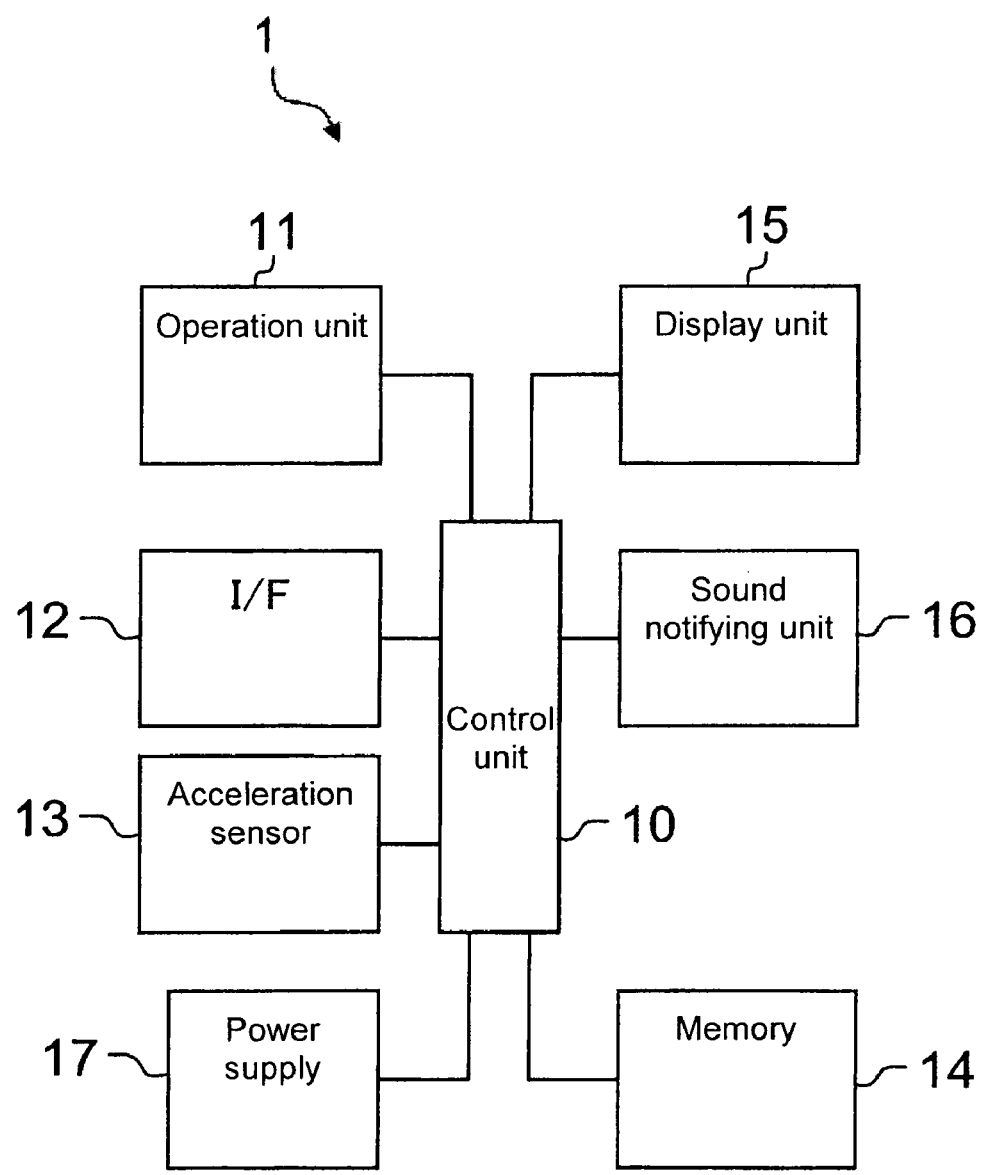
FIG. 1 is a block diagram showing an internal configuration of an activity meter.

1 Activity meter
10 Control unit
11 Operation unit
12 I/F
13 Acceleration sensor
14 Memory
15 Display unit
16 Sound notifying unit
17 Power supply

BEST MODE FOR CARRYING OUT THE INVENTION

Preferred embodiments of the present invention will be illustratively described in detail below with reference to the drawings.

<Configuration of Activity Meter>

FIG. 1 is a block diagram showing an internal configuration of an activity meter. The activity meter 1 includes a control unit 10, an operation unit 11, an I/F 12, an acceleration sensor 13, a memory 14, a display unit 15, a sound notifying unit 16, a power supply 17, and the like.

The control unit 10 is configured by a microcomputer and the like, and is responsible for the function of executing various types of calculation processes such as detection of the physical activity, calculation and recording of the physical activity amount, and display of implementing state, as well as control of the display unit 15 and the sound notifying unit 16 according to a program stored in advance. The details on the function of the control unit 10 will be hereinafter described.

The operation unit 11 is a user interface for performing operations such as setting of goal, reset of number of steps and display, and input of various set values. The I/F 12 is an external interface for transmitting and receiving data with an external device such as a body composition monitor and a personal computer through wireless communication or wired communication. The memory 14 is non-volatile storage means for storing the number of steps, the implementing condition and the goal value of the physical activity amount, the information related to a user, various set values used in a program, the calculation formula (coefficient), data such as a table, and the like. The display unit 15 is display means configured by an LCD (Liquid Crystal Display) and the like, and displays information such as number of steps, implementing condition and goal attainment level of physical activity, and the like. The sound notifying unit 16 is a function for ringing an operation sound, a walking pitch sound, an alarm sound and the like according to the control of the control unit 10.

<Acceleration Sensor>

The acceleration sensor 13 is a three-axes acceleration sensor capable of detecting the acceleration in three directions orthogonal to each other. When the activity meter 1 is attached to a user in a predetermined attachment mode, the acceleration sensor 13 takes an orientation capable of detecting the acceleration in three directions of a vertical direction (up and down direction) and two horizontal directions (front and back direction and left and right direction). Sensors of any principle such as an electrostatic capacity sensor and a piezoelectric sensor can be used for the acceleration sensor 13.

Figure 2:
FIG. 2A is a sensor output signal (raw signal) during a laundry hanging operation.
FIG. 2B is a signal of after passing a 1 Hz high-pass filter.
Figure 2:
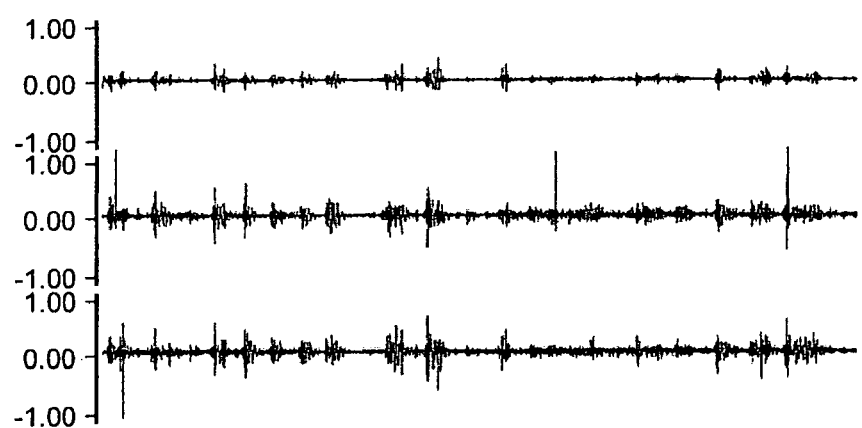

FIG. 2A and FIG. 2B show one example of an output signal of the acceleration sensor 13 of electrostatic capacity type. FIG. 2A is a sensor output signal (raw signal) during the laundry hanging operation, and FIG. 2B is a signal of after passing a 1 Hz high-pass filter. The acceleration signals in the up and down direction, the front and back direction, and the left and right direction are shown in order from the top.

As shown in FIG. 2A, the acceleration signal in the up and down direction of the raw signal contains a DC component corresponding to a gravitational acceleration (−1.0 G). The acceleration signals of all directions contain a low frequency component corresponding to the fluctuation of the gravitational acceleration (static acceleration). Therefore, if the raw signal is used as is, the fluctuation of the acceleration is over-evaluated, and the exercise intensity cannot be accurately calculated. In particular, since the orientation of tilting or bending the upper body is often taken, and the change in tile of the acceleration sensor 13 is large in operations such as hanging laundry, the fluctuation component of the static acceleration cannot be ignored.

Thus, the low frequency component (fluctuation component of static acceleration) contained in the output signal of the sensor is desirably removed using a high-pass filter, as shown in FIG. 2B. It can be seen that only the component of the dynamic acceleration caused by the body motion of the user remains in the signal of after passing the high-pass filter. Through the use of such a signal, the body motion of the user can be accurately grasped, and the acceleration and the exercise intensity can be accurately evaluated.

The acceleration of a type of detecting only the change in the dynamic acceleration without detecting the change in the static acceleration, such as the piezoelectric sensor, may be used. In this case, the raw signal output from the sensor can be used as is for the calculation of the acceleration and the exercise intensity, and thus the configuration such as the high-pass filter is unnecessary and the cost can be reduced.

<Calculation of Acceleration>

Figure 3:
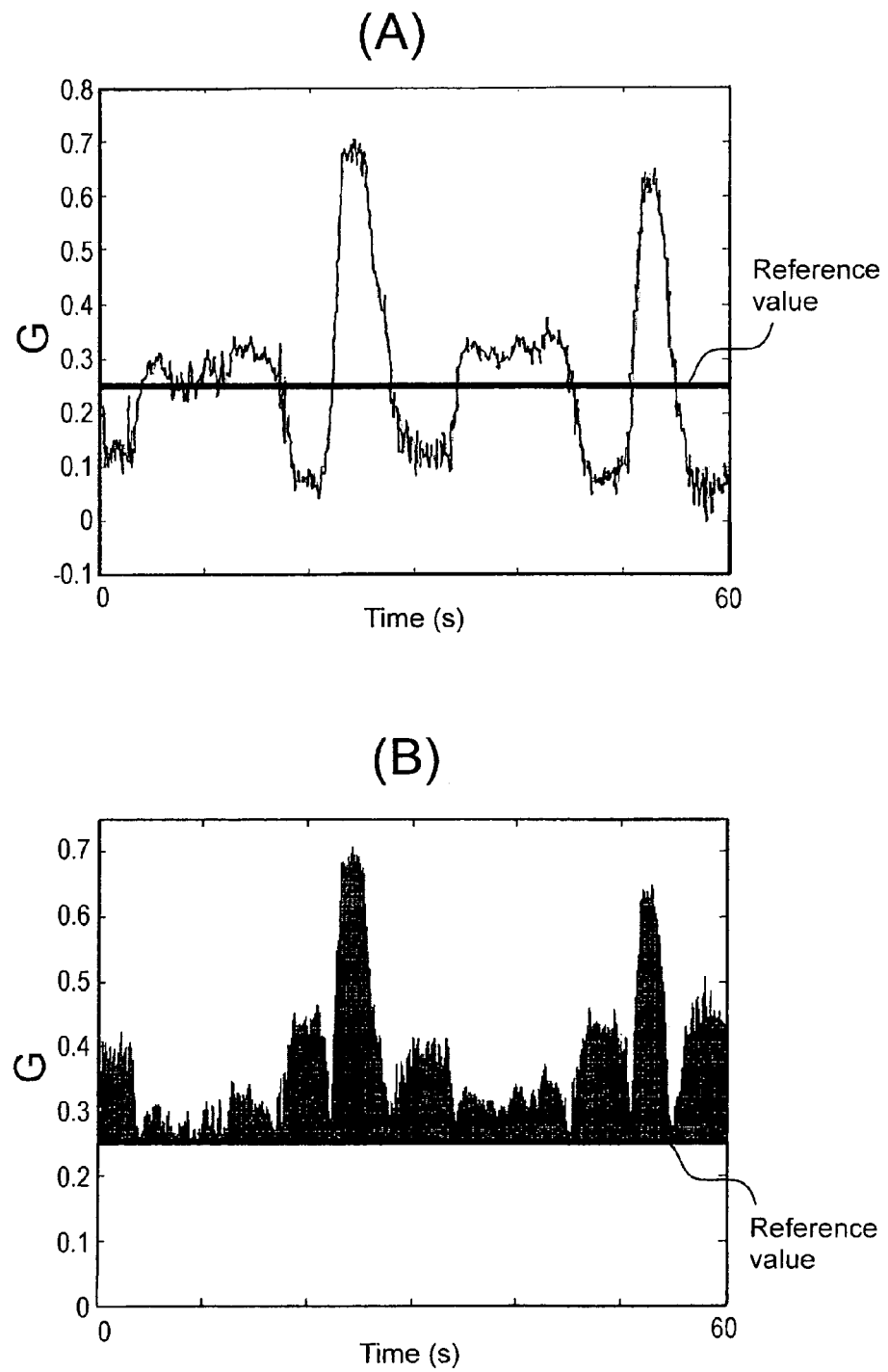
FIG. 3A and FIG. 3B are diagrams each showing a method of calculating the value of acceleration from the output signal of the sensor.

FIG. 3A and FIG. 3B show a method of calculating the value of acceleration from the output signal of the sensor. As shown in FIG. 3A, since the magnitude of the acceleration is constantly fluctuating, there is no significance in adopting an instantaneous value at a certain time point. The output signals of a predefined period (unit period) are thus statistically processed to obtain a representative value of the magnitude of the acceleration in the relevant unit period.

In the present embodiment, about 2000 samplings are performed from signals of 60 seconds. An arithmetic average (reference value) of the sampling values is then calculated, as shown in FIG. 3A. Then, as shown in FIG. 3B, absolute values of a difference (deviation) between the sampling value and the reference value are calculated, and the arithmetic average of the absolute values of the deviation is obtained. The arithmetic average of the absolute value of the deviation is a statistics value called an average deviation, where such a value is used as a representative value of the acceleration in the unit period (60 seconds) in the present embodiment.

The representative value (average deviation) of the acceleration is calculated for the up and down direction, the left and right direction, and the front and back direction. In the following equation, X is the representative value of the acceleration in the up and down direction, Y is the representative value of the acceleration in the left and right direction, and Z is the representative value of the acceleration in the front and back direction. Furthermore, xi, yi, and zi are sampling values, ax, ay, and az are arithmetic averages of the sampling values, and N is the number of samples.

$$X = \frac{\sum_{i}^{N} |a_x - x_i|}{N}$$

$$Y = \frac{\sum_{i}^{N} |a_y - y_i|}{N}$$

$$Z = \frac{\sum_{i}^{N} |a_z - z_i|}{N}$$

(Equation 1)

After the representative values X, Y, and Z of the acceleration in each direction are obtained, the representative values are synthesized to calculate the synthesized acceleration S (corresponding to "representative acceleration" of the present invention) of three axes. The vertical component Sv and the horizontal component Sh of the synthesized acceleration S are expressed with the following equations.

$$S = \sqrt{X^2 + Y^2 + Z^2}$$

$$Sv = \sqrt{X^2}$$

$$Sh = \sqrt{Y^2 + Z^2}$$

(Equation 2)

<Calculation of Exercise Intensity>

The exercise intensity is calculated from the synthesized acceleration S. Specifically, the synthesized acceleration S is converted to exercise intensity using a calculation formula (conversion formula) obtained in advance through experiments.

Figure 4:
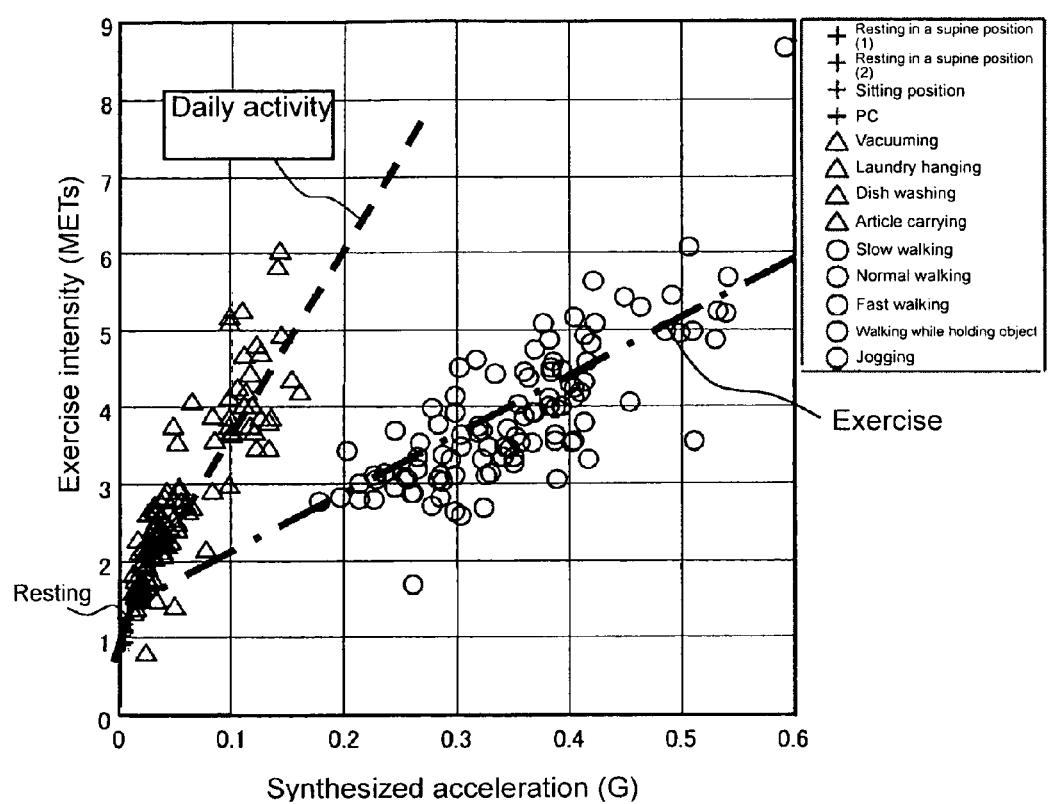
FIG. 4 is a diagram showing a relationship between synthesized acceleration and the exercise intensity obtained through experiments.

FIG. 4 shows a relationship between the synthesized acceleration and the exercise intensity obtained through experiments. The horizontal axis is the synthesized acceleration [G] and the vertical axis is the exercise intensity [METs]. The measurement results for resting in a supine position, sitting position, and working on a personal computer (PC) are shown as data of resting. The measurement results for vacuuming operation, laundry hanging operation, dish washing operation, and article carrying operation are shown as data of daily activity. Furthermore, measurement results for slow walking, normal walking, fast walking, walking while holding an object, and jogging are shown as data of exercise.

As apparent from FIG. 4, the distributions of the data of resting, daily activity, and exercise shows tendencies different from each other. Thus, in the present embodiment, the physical activity is classified into three categories, "resting", "daily activity", and "exercise", and a regression line (or regression curve) is obtained from the respective experimental data. The regression line (or regression curve) is a calculation formula for converting the synthesized acceleration to the exercise intensity. The respective calculation formula (coefficient) of resting, daily activity, and exercise is stored in the memory 14 of the activity meter 1.

Figure 5:
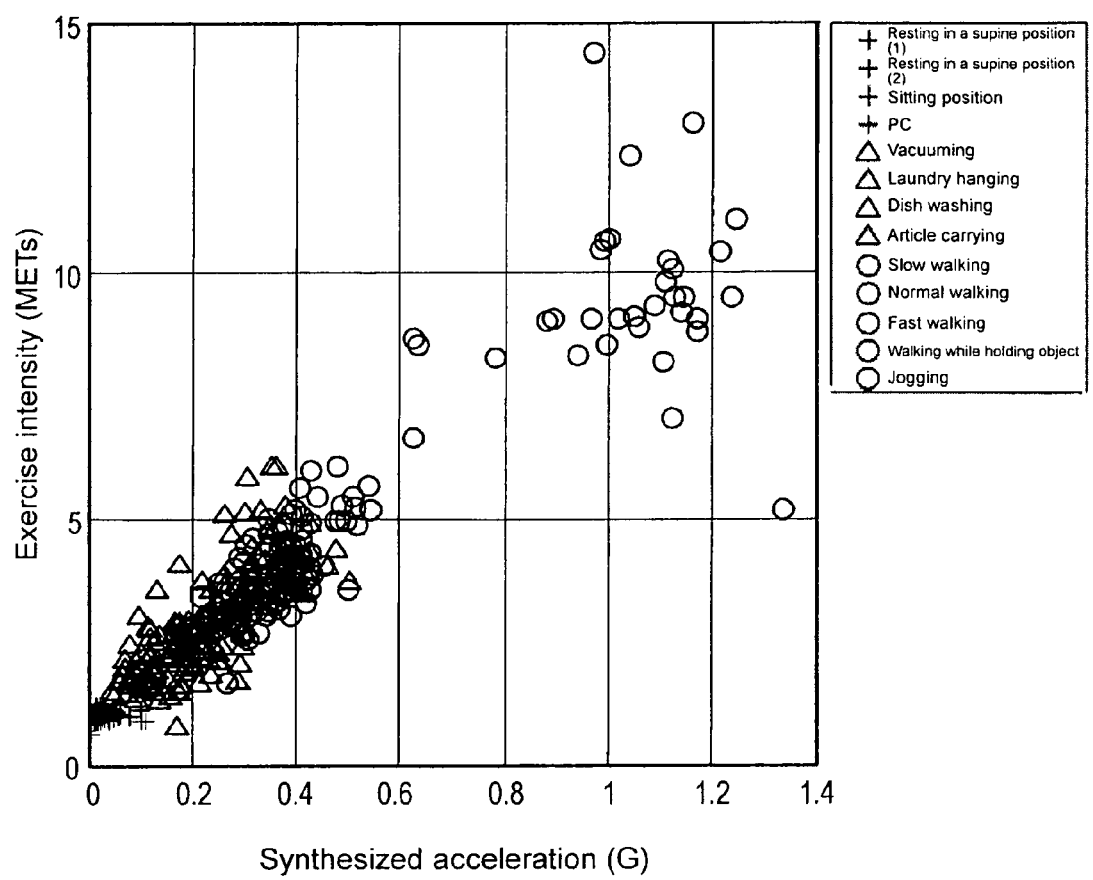
FIG. 5 is a diagram showing synthesized acceleration obtained from the signal of before passing the high-pass filter.

The synthesized acceleration of FIG. 4 is a value obtained from the signal of after passing the high-pass filter (i.e., signal removed with fluctuation component of gravitational acceleration). As a comparative example, FIG. 5 shows a synthesized acceleration obtained from the signal of before passing the high-pass filter. In FIG. 5, the isolation of the data of resting, daily activity, and exercise is not satisfactory, and the acceleration and the exercise intensity are difficult to accurately evaluate. In particular, in the case of the operation with large fluctuation in the gravitational acceleration as in the daily activity, portions where the order of the magnitude of the synthesized acceleration and the magnitude of the exercise intensity is reversed are found. Thus, it is apparent that removing the fluctuation component of the gravitation acceleration is effective.

<Determination of Physical Activity and Selection of Calculation Formula>

As described above, the activity meter 1 of the present embodiment has a plurality of calculation formulas according to the type of physical activity. During the operation, the activity meter 1 automatically determines the type of physical activity based on the output signal of the acceleration sensor 13, and selects an appropriate calculation formula.

Specific operation examples in the determination of the physical activity and the selection of the calculation formula will be described below.

FIRST OPERATION EXAMPLE

Figure 6:
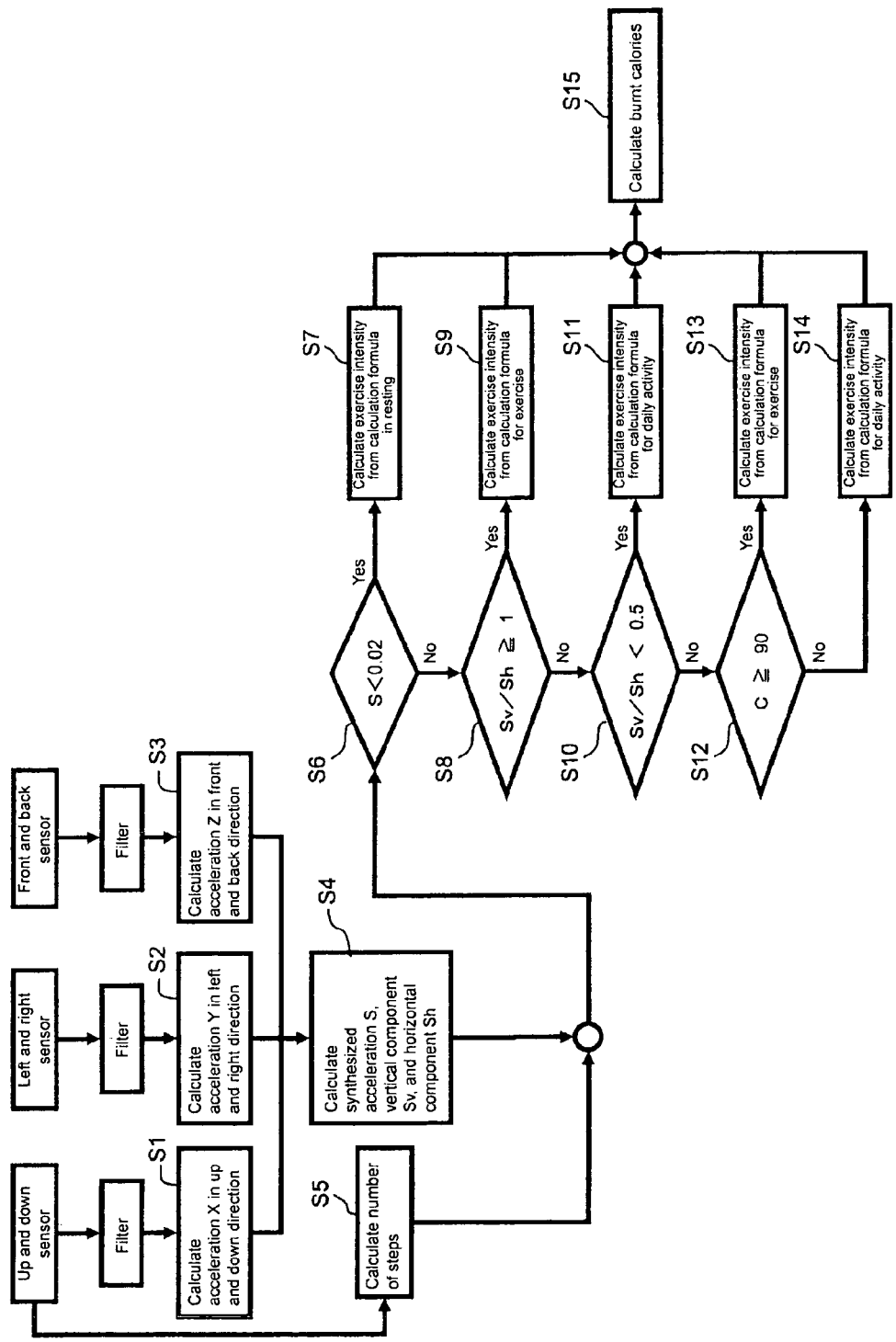
FIG. 6 is a flowchart showing a first operation example of the activity meter.

FIG. 6 is a flowchart showing a first operation example of the activity meter 1. In the first operation example, the activity meter 1 determines the type of physical activity based on the "number of steps" and the "ratio of horizontal component and vertical component of synthesized acceleration", and determines the calculation formula to use. The signal processing shown in FIG. 6 is executed by the control unit 10.

First, the control unit 10 calculates the representative values X, Y, and Z of the acceleration in each direction of up and down, left and right, and front and back in unit period according to the above-mentioned acceleration calculation method (steps S1 to S3), and calculates the synthesized acceleration S and the vertical component Sv and the horizontal component Sh thereof (step S4).

The control unit 10 obtains the number of steps C in the unit period based on the acceleration signal in the up and down direction (step S5). Specifically, the number of steps C is obtained by counting the number of times the value of the acceleration in the up and down direction exceeded a predetermined value.

The control unit 10 then examines whether or not the value of the synthesized acceleration S is greater than or equal to the threshold value 0.02 (step S6). If the value of the synthesized acceleration S is smaller than 0.02, the control unit 10 judges that "user is in a resting state", and reads out the calculation formula in resting from the memory 14. The control unit 10 then calculates the exercise intensity from the synthesized acceleration S using the calculation formula in resting (step S7). If the value of the synthesized acceleration S is greater than or equal to 0.02, the process proceeds to step S8.

In step S8, the control unit 10 obtains the value of the ratio Sv/Sh of the vertical component Sv with respect to the horizontal component Sh of the synthesized acceleration, and examines whether or not the ratio Sv/Sh is greater than or equal to the threshold value 1.0. If the ratio Sv/Sh is greater than or equal to 1.0, the control unit 10 judges that "physical activity of the user is exercise", and reads out the calculation formula for exercise from the memory 14. The control unit 10 then calculates the exercise intensity from the synthesized acceleration S using the calculation formula for exercise (step S9). If the ratio Sv/Sh is smaller than 1.0, the process proceeds to step S10.

In step S10, the control unit 10 examines whether or not the ratio Sv/Sh is smaller than the threshold value 0.5. If the ratio Sv/Sh is smaller than 0.5, the control unit 10 judges that "physical activity of the user is daily activity", and reads out the calculation formula for daily activity from the memory 14. The control unit 10 then calculates the exercise intensity from the synthesized acceleration S using the calculation formula for daily activity (step S11). If the ratio Sv/Sh is greater than or equal to 0.5, the process proceeds to step S12.

In step S12, the control unit 10 examines whether or not the number of steps C is greater than or equal to the threshold value 90. If the number of steps C is greater than or equal to 90, the control unit 10 judges that "physical activity of the user is exercise", and calculates the exercise intensity using the calculation formula for exercise (step S13), similar to step S9. If the number of steps C is smaller than 90, the exercise intensity is calculated using the calculation formula for daily activity (step S14), similar to step S11.

After the exercise intensity is calculated with any one of the calculation formulas, the control unit 10 calculates burnt calories from the exercise intensity (step S15). The conversion from the exercise intensity (METs) to the burnt calories may use a known method. The exercise intensity and the burnt calories measured in such a manner are then recorded in the memory 14. The user can check the measured and recorded exercise intensity and the burnt calories on the display unit 15.

Figure 7:
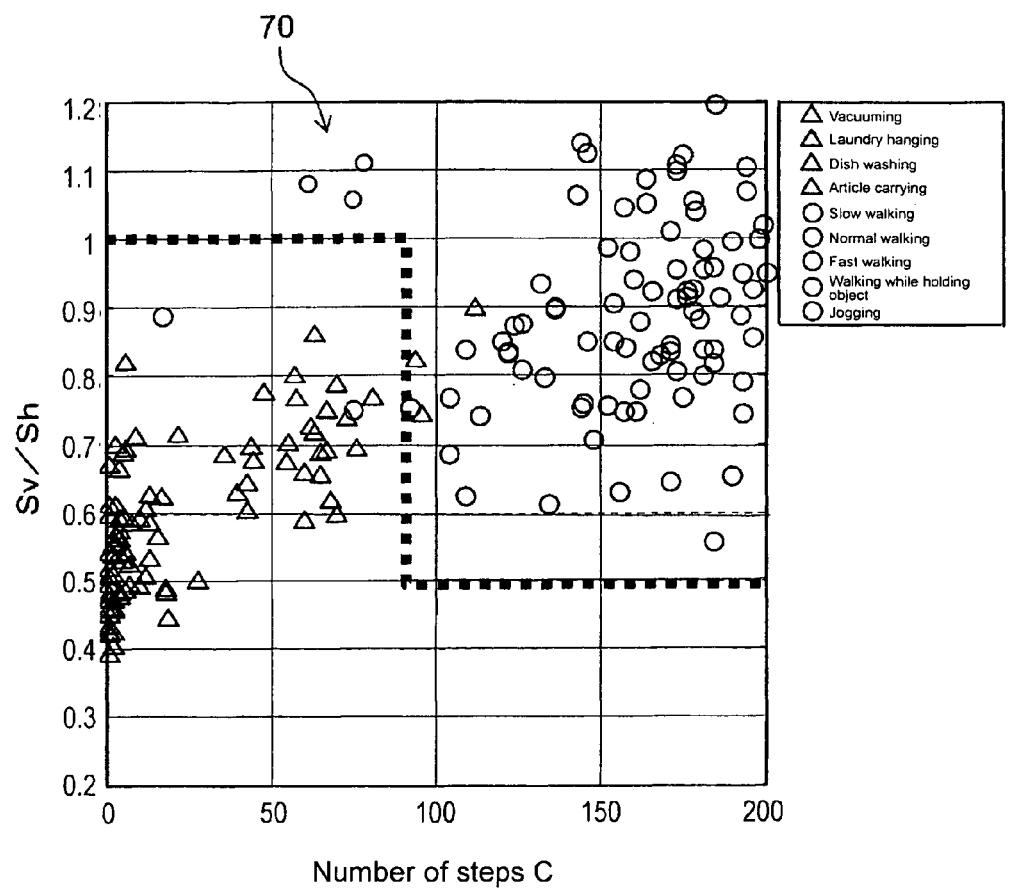
FIG. 7 is a diagram showing the result of a verification experiment of a determination method of the first operation example.

FIG. 7 shows the result of the verification experiment of the determination method of the first operation example. The horizontal axis of FIG. 7 is the number of steps C in unit period (60 seconds), and the vertical axis is the ratio Sv/Sh. The measurement data (triangle) of the daily activity and the measurement data (circle) of the exercise were plotted in such space, and the respective distributions were found to be clearly separated.

As a general tendency, the exercise has a larger value of ratio Sv/Sh than the daily activity. This is because many changes in orientation are made to front and back, and left and right in the daily activity such as cleaning and doing laundry, where as the operation of repeating the up and down motion with the same orientation is mainly carried out in the exercise such as walking. The number of steps C tends to be greater in the exercise performed in a planned and intended manner than in the daily activity. However, such tendencies in the ratio Sv/Sh and the walking C are not necessarily applied to all cases. For instance, an interval training of walking 30 seconds and resting 30 seconds has small number of steps C but is to be classified in exercise (see reference number 70 in FIG. 7). Thus, the daily activity and the exercise are difficult to accurately separate with only the evaluation of either the ratio Sv/Sh or the number of steps C.

In the determination method of the first operation example, the determination conditions combining the ratio Sv/Sh and the number of steps C are used, as described above. Separating the measurement data with the determination condition (see broken line in FIG. 7) shown in steps S8, S10, and S12 of FIG. 6, the daily activity and the exercise were classified at an accuracy rate of substantially 100%.

SECOND OPERATION EXAMPLE

Figure 8:
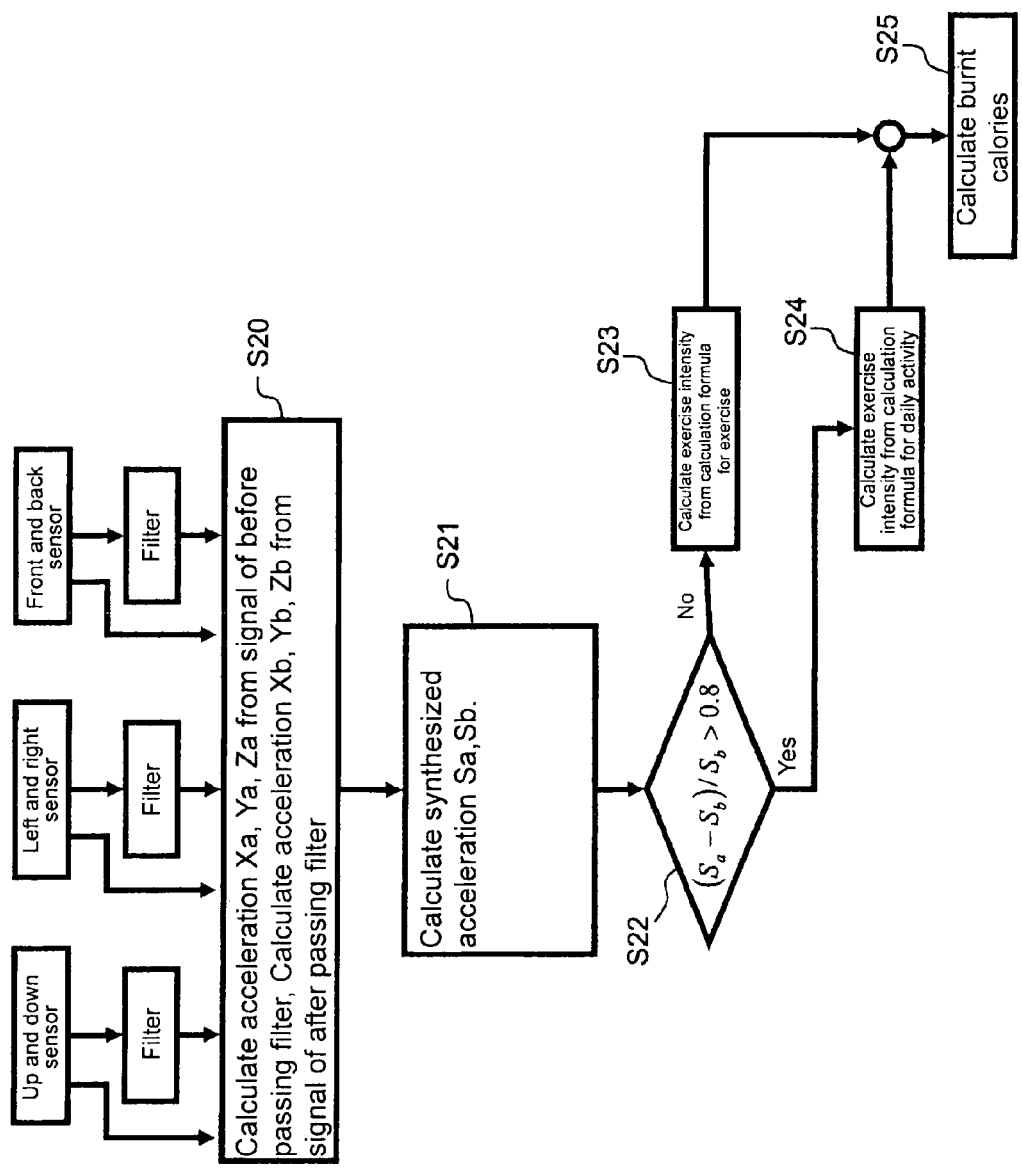
FIG. 8 is a flowchart showing a second operation example of the activity meter.

FIG. 8 is a flowchart showing a second operation example of the activity meter. In the second operation example, the activity meter 1 determines the type of physical activity based on the change in tilt of the body, and determines the calculation formula to use. The signal processing shown in FIG. 8 is executed by the control unit 10.

First, the control unit 10 calculates the representative values of the acceleration in each direction of up and down, left and right, and front and back in unit period according to the above-mentioned acceleration calculation method (step S20). In this case, the control unit 10 calculates the representative values Xa, Ya, and Za of the acceleration from the signal of before passing the high-pass filter, and calculates the representative values Xb, Yb, and Zb of the acceleration from the signal of after passing the high-pass filter. The control unit 10 then calculates the synthesized acceleration Sa from the representative values Xa, Ya, and Za and the synthesized acceleration Sb from the representative values Xb, Yb, and Zb (step S21). The synthesized acceleration Sa corresponds to a first representative acceleration of the present invention and the synthesized acceleration Sb corresponds to a second representative acceleration.

The control unit 10 calculates an evaluation value expressed as (Sa−Sb)/Sb (step S22). The value of the synthesized acceleration Sa contains the fluctuation component of both the dynamic acceleration and the static acceleration (gravitational acceleration), whereas the value of the synthesized acceleration Sb only contains the fluctuation component of the dynamic speed. The difference (Sa−Sb) of the two can be referred to as a value representing the fluctuation component of the static acceleration, and the synthesized acceleration Sb can be referred to as a value representing the fluctuation component of the dynamic acceleration. The evaluation value (Sa−Sb)/Sb corresponds to the ratio of the value representing the fluctuation component of the static acceleration and the value representing the fluctuation component of the dynamic acceleration. The evaluation value (Sa−Sb)/Sb is the value (index) representing the change in tile of the body.

The control unit 10 examines whether or not the evaluation value is greater than the threshold value 0.8 (step S22). If the evaluation value is smaller than or equal to 0.8, the control unit 10 judges that "physical activity of the user is exercise", and reads out the calculation formula for exercise from the memory 14. The control unit 10 then calculates the exercise intensity from the synthesized acceleration Sb using the calculation formula for exercise (step S23).

If the evaluation value is greater than 0.8, the control unit 10 judges that "physical activity of the user is daily activity", and reads out the calculation formula for daily activity from the memory 14. The control unit 10 then calculates the exercise intensity from the synthesized acceleration Sb using the calculation formula for daily activity (step S24).

After the exercise intensity is calculated with any one of the calculation formulas, the control unit 10 calculates the burnt calories from the exercise intensity (step S25). In the flowchart of FIG. 8 as well, whether or not resting may be determined based on the value of the synthesized acceleration Sb, similar to the flowchart of FIG. 6.

Figure 9:
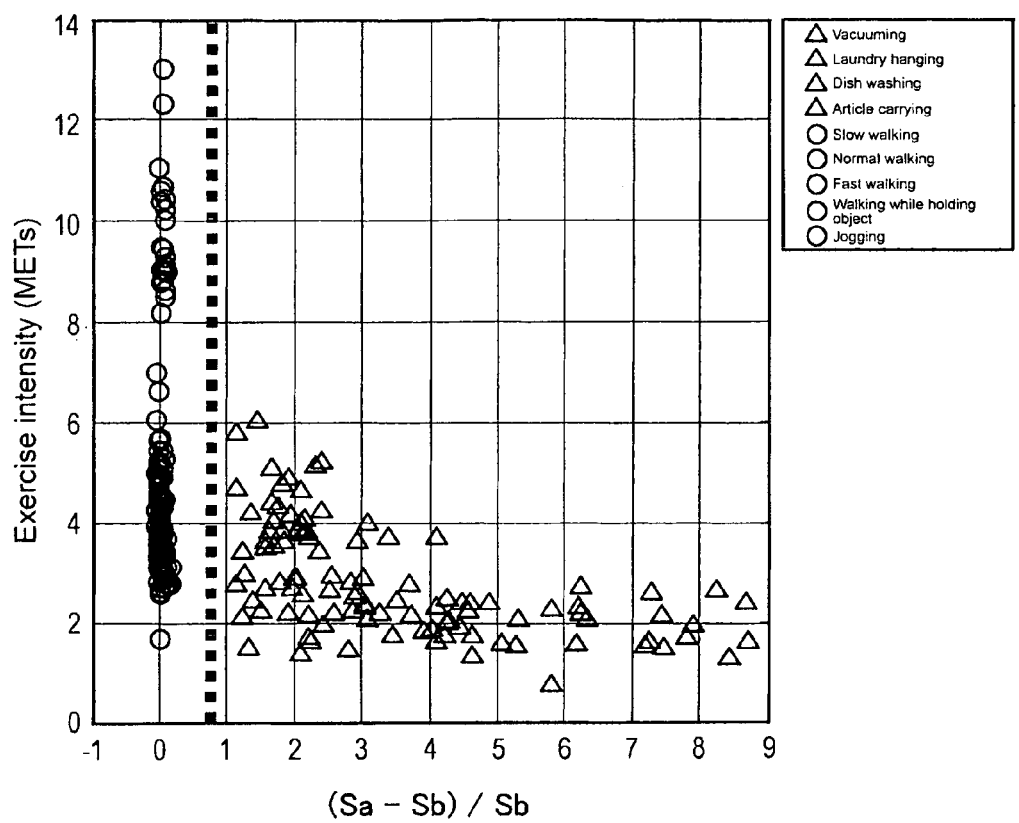
FIG. 9 is a diagram showing the result of a verification experiment of a determination method of the second operation example.

FIG. 9 shows the result of the verification experiment of the determination method of the second operation example. The horizontal axis of FIG. 9 is the evaluation value (Sa−Sb)/Sb, and the vertical axis is the exercise intensity. The measurement data (triangle) of the daily activity and the measurement data (circle) of the exercise were plotted in such space, and the respective distributions were found to be clearly separated.

In the case of exercise such as walking and jogging, the tilt of the body (orientation of the sensor) barely changes. That is, the output signal of the sensor barely contains the fluctuation component of the static acceleration. Thus, in the case of exercise, the synthesized accelerations Sa and Sb show substantially the same value, and the evaluation value (Sa−Sb)/Sb becomes substantially zero.

In the case of the daily activity such as cleaning and doing laundry, the operation of tilting or bending the upper body is performed, and thus many changes are made in the tilt of the body (orientation of the sensor), and the fluctuation of the static acceleration (gravitational acceleration) appears in the output signal of the sensor. Thus, a significant difference creates between the synthesized accelerations Sa and Sb, and the evaluation value (Sa−Sb)/Sb becomes large.

Separating the measurement data with the determination condition (threshold value 0.8) shown in FIG. 8, the daily activity and the exercise were classified at an accuracy rate of substantially 100%.

As described above, the activity meter 1 of the present embodiment can determine the type of physical activity with satisfactory accuracy based on the output signal of the acceleration sensor, and select an appropriate calculation formula. Since the physical activity amount (exercise intensity, burnt calories) is calculated using an appropriate calculation formula, the activity amount can be measured with satisfactory accuracy for various types of physical activities from daily activity to exercise.

The configuration of the embodiments described above merely illustrates one specific example of the present invention. The scope of the present invention is not limited to the above-described embodiment, and various modifications may be made within the scope of the technical idea thereof.

For instance, the specific configuration of the procedure (flow) of determination, threshold value, evaluation value, and the like is not limited to those illustrated in the first and second operation examples, and may be appropriately modified. In the above-described embodiment, the physical activity is classified into three categories of resting, daily activity, and exercise, but the daily activity and the exercise may be further segmentalized. The number of categories and the calculation formula for each category can be appropriately set by analyzing the experiment results shown in FIG. 4. In the first operation example, the ratio Sv/Sh is used for the valuation of the vertical component Sv and the horizontal component Sh of the synthesized acceleration S, but any index may be used as long the vertical component and the horizontal component can be compared. For instance, indices such as Sv−Sh, Sv/S, and Sh/S may be used. Furthermore, in the first operation example, high determination accuracy is realized by using two indices of the ratio Sv/Sh and the number of steps, but only either one of the indices may be used if a simple determination is to be performed. Alternatively, the determination accuracy may be further enhanced by combining three or more indices. In the second operation example, the evaluation value (Sa−Sb)/Sb is used for the "value representing change in tilt of the body", but other indices such as Sa−Sb and Sa/Sb may be used as a value representing change in tilt of the body. The index obtained from the vertical component Sv and the horizontal component Sh of the synthesized acceleration S, as used in the first operation example, may be used as the "value representing change in tilt of the body" in the second operation example.

Since the energy expenditure differs among individuals even if the content of the exercise is the same, variation may possibly occur in the exercise effect that is actually obtained. The intensity may be corrected based on the personal attribute of the user. The personal attribute that may influence the energy expenditure includes sex, age, height, BMI, body composition value, and basal metabolism rate. The magnitude the value of the personal attribute influences the energy expenditure can be confirmed through clinical tests. The correction coefficient for the value of the personal attribute or every layer may be defined and included in the calculation formula of the intensity, so that the difference in exercise effect due to the difference in personal attribute can be appropriately corrected.

The invention claimed is:

1. An activity meter comprising:
    a sensor for detecting acceleration in a plurality of directions;
    representative acceleration calculation means for calculating a representative acceleration, which is a representative value of the acceleration in a unit period, based on an output signal of the sensor; and
    exercise intensity calculation means for calculating an exercise intensity of a body motion performed in the unit period from the representative acceleration; wherein
    the exercise intensity calculation means includes a plurality of calculation formulas to use in the calculation of the exercise intensity, and determines if a type of the body motion performed in the unit period is exercise or a daily activity based on a horizontal component and a vertical component of the representative acceleration, and changes the calculation formula to use in the calculation of the exercise intensity for the exercise and for the daily activity.

2. The activity meter according to claim 1, wherein the exercise intensity calculation means determines if a type of the body motion performed in the unit period is exercise or a daily activity based on a ratio of the horizontal component and the vertical component of the representative acceleration, and changes the calculation formula to use in the calculation of the exercise intensity for the exercise and for the daily activity.

3. The activity meter according to claim 1, wherein the exercise intensity calculation means determines if a type of the body motion performed in the unit period is exercise or a daily activity based on a difference between the horizontal component and the vertical component of the representative acceleration, and changes the calculation formula to use in the calculation of the exercise intensity for the exercise and for the daily activity.

4. The activity meter according to claim 1, further comprising:
    number of steps calculation means for calculating number of steps in the unit period based on the output signal of the sensor; wherein
    the exercise intensity calculation means determines if a type of the body motion performed in the unit period is exercise or a daily activity based on the number of steps, as well as the horizontal component and the vertical component of the representative acceleration, and changes the calculation formula to use in the calculation of the exercise intensity for the exercise and for the daily activity.

5. The activity meter according to claim 4, wherein
    the exercise intensity calculation means includes at least a calculation formula for the exercise and a calculation formula for the daily activity for the calculation formula;
    the calculation formula for the exercise is selected when a value of a ratio of the vertical component with respect to the horizontal component of the representative acceleration is greater than or equal to a first threshold value;
    the calculation formula for the daily activity is selected when the value of the ratio is smaller than a second threshold value; and
    the calculation formula for the exercise or the calculation formula for the daily activity is determined depending on whether or not the number of steps is greater than or equal to a third threshold value when the value of the ratio is greater than or equal to the second threshold value and smaller than the first threshold value.

6. The activity meter according to claim 1, comprising a filter for removing a fluctuation component of a static acceleration from the output signal of the sensor.

7. The activity meter according to claim 1, wherein the sensor is a sensor that does not detect change in a static acceleration and detects only change in a dynamic acceleration.

8. An activity meter comprising:
a sensor for detecting acceleration in a plurality of directions;
representative acceleration calculation means for calculating a representative acceleration, which is a representative value of the acceleration in a unit period, based on an output signal of the sensor; and
exercise intensity calculation means for calculating an exercise intensity of a body motion performed in the unit period from the representative acceleration; wherein
the exercise intensity calculation means includes a plurality of calculation formulas to use in the calculation of the exercise intensity, and determines if a type of the body motion performed in the unit period is exercise or a daily activity based on change in tilt of a body, and changes the calculation formula to use in the calculation of the exercise intensity for the exercise and for the daily activity.

9. The activity meter according to claim 8, wherein the exercise intensity calculation means determines a value representing the change in the tilt of the body based on a value representing a fluctuation component of a static acceleration and a value representing a fluctuation component of a dynamic acceleration contained in the output signal of the sensor.

10. The activity meter according to claim 8, comprising:
a filter for removing a fluctuation component of a static acceleration from the output signal of the sensor; wherein
a first representative acceleration is calculated from an output signal of before passing the filter;
a second representative acceleration is calculated from an output signal of after passing the filter; and
a value representing the change in the tilt of the body is determined based on the first representative acceleration and the second representative acceleration.

11. The activity meter according to claim 9, wherein
the exercise intensity calculation means includes at least a calculation formula for the exercise and a calculation formula for the daily activity for the calculation formula;
the calculation formula for the exercise is selected when the value representing the change in the tilt of the body is smaller than a fourth threshold value; and
the calculation formula for the daily activity is selected when the value representing the change in the tilt of the body is greater than or equal to the fourth threshold value.

12. The activity meter according to claim 8, wherein the value representing the change in the tilt of the body is determined based on a horizontal component and a vertical component of the representative acceleration.

13. The activity meter according to claim 1, wherein
the exercise intensity calculation means includes a calculation formula for resting for the calculation formula; and
the exercise intensity is calculated using the calculation formula for resting when the representative acceleration is smaller than a fifth threshold value.

* * * * *